United States Patent [19]

Elmvist

[11] Patent Number: 5,253,644
[45] Date of Patent: Oct. 19, 1993

[54] PMT DETECTING PACEMAKER

[75] Inventor: Hakan Elmvist, Bromma, Sweden

[73] Assignee: Siemens Aktiengesellschaft, Munich, Fed. Rep. of Germany

[21] Appl. No.: 752,649
[22] PCT Filed: Sep. 8, 1989
[86] PCT No.: PCT/SE89/00484
  § 371 Date: Aug. 23, 1991
  § 102(e) Date: Aug. 23, 1991
[87] PCT Pub. No.: WO91/03274
  PCT Pub. Date: Mar. 21, 1991

[51] Int. Cl.⁵ .......................................... A61N 1/368
[52] U.S. Cl. ............................................ 607/14
[58] Field of Search ................... 128/449 PG, 419 PT

[56] References Cited

U.S. PATENT DOCUMENTS

| | | | |
|---|---|---|---|
| 4,381,786 | 5/1983 | Duggan | 128/419 PG |
| 4,515,161 | 5/1985 | Wittkampf et al. | |
| 4,569,350 | 2/1986 | Mumford et al. | |
| 4,577,634 | 3/1986 | Gessman | |
| 4,606,350 | 8/1986 | Frost | 128/419 PG |
| 4,781,194 | 11/1988 | Elmqvist | 128/419 PG |
| 4,890,617 | 1/1990 | Markowitz et al. | 128/419 PG |

FOREIGN PATENT DOCUMENTS 0118780 9/1984 European Pat. Off. .
0318304 5/1989 European Pat. Off. .

OTHER PUBLICATIONS

"Merits of various Antipacemaker Circus Movement Tachycardia Features," Den Dulk et al. PACE, vol. 9, Nov-Dec. 1986, pp. 1055–1062.
"Spontaneous Endless Loop Tachycardia," Oseran et al., PACE vol. 9, May-Jun., 1986, pp. 379–386.

Primary Examiner—William E. Kamm
Attorney, Agent, or Firm—Hill, Steadman & Simpson

[57] ABSTRACT

A pacemaker-mediated tachycardia (PMT) is detected by calculating the correlations for typically two to six heart cycles between, for example, spontaneous atrial beats (PP-intervals) and the pacemaker generated AV delays, which are varied in a predictable manner. The correlation is low when no PMT is present because the possible variation in the interval between spontaneous atrial beats is independent of the variation of the AV delay. Correlation is high when a PMT is present, because the interval between spontaneous atrial beats will then equal the PMT cycle time, i.e., the AV delay plus the retrograde conduction time in the heart tissue.

10 Claims, 2 Drawing Sheets

PMT DETECTING PACEMAKER

BACKGROUND OF THE INVENTION

1. Field of the Invention

The present invention relates to a heart pacemaker, and in particular to a heart pacemaker comprising means for detecting a pacemaker-mediated tachycardia.

2. Description of the Prior Art

Atrial synchronized pacing systems include an atrial (P-wave) sensing circuit, which, in connection with retrograde (ventriculoatrial, VA) heart tissue electrical conduction might cause a so called pacemaker-mediated tachycardia (PMT). A PMT results when the atrial sensing circuit detects a P-wave induced by e.g. a retrogradely conducted ventricular activity outside the sensing circuit's refractory periods and the pacemaker subsequently initiates a paced ventricular beat. Repeated stimulation is sustained by heart tissue retrograde conduction and by pacemaker antegrade conduction.

Although this complication is related to atrial synchronized systems in general, it can be exemplified with reference to dual chamber (DDD) pacemakers. With the advent of the first generation of such pacemakers with relatively short atrial refractory periods, PMT was identified as a significant problem, and later generations of such pacemakers therefore include methods for preventing PMT.

One such known method involves the use of programmable atrial refractory periods, where the atrial refractory period is programmed to be longer than the retrograde conduction interval. However, this method lowers the upper synchronized rate limit of the pacemaker and, in patients with a long retrograde conduction interval, the refractory period required is so long that the advantages of dual chamber pacing are seriously affected. Another known method is based on the fact that the majority of PMT is initiated by ventricular premature beats (VPB), viz. a ventricular event not preceded by an atrial beat. Therefore, this known method foresees that only a VPB triggers a prolonged atrial refractory period. Alternatively, a VPB could trigger a simultaneous atrial stimulation causing the atrium to be refractory when the retrograde conduction occurs. However, although this method generally allows shorter refractory periods, PMT remains a problem in patients where the initiating mechanism for PMT is unknown or is different from a VPB (Spontaneous Endless Loop Tachycardia by Oseran et al, PACE vol. 9, May–June 1986, pages 379 to 386).

Further, it is known that a PMT, once established, can for instance be terminated by omitting ventricular beats or delivering critically timed ventricular premature beats. Here, however, PMT detection is critical, and a possible detection criterion such as a stable high frequency at, or in the vicinity of, the upper rate pacing limit cannot be reliably related to a PMT (Merits of Various Antipacemaker Circus Movement Tachycardia Features by den Dulk et al, PACE, vol. 9, November–December, Part II 1986).

SUMMARY OF THE INVENTION

The object of the present invention is therefore to provide for a reliable PMT detecting device.

The above object is achieved in accordance with the principles of the present invention in a cardiac pacemaker including a sensor which detects natural and stimulated atrial events, means for stimulating the ventricle, and a variable delay circuit which generates a variable time delay between the detection of an atrial event and the stimulation of the ventricle. The pacemaker also includes a measuring circuit which measures the time interval between consecutive detected events, at least one of the detected events being a naturally occurring heart beat. A calculating unit is provided which calculates the correlation between the time delay and the measured time interval. A logic circuit is provided which, based on the degree of correlation between the time delay and the measured time interval determines whether a pacemaker-mediated tachycardia is present. This decision can be made, for example, by assuming that a pacemaker-mediated tachycardia is present whenever the value of the correlation deviates from a predetermined value.

Further protection can be added in an embodiment of the invention wherein a second predetermined value is entered into the logic circuit, and a decision is made that pacemaker-mediated tachycardia is not present if the value of the correlation falls below the second predetermined value, the second predetermined value being lower than the first predetermined value.

The correlation calculation can be undertaken over a number, for example at least two, heart cycles. The measured time interval may be, for example, the time interval between consecutive P-waves.

DESCRIPTION OF THE DRAWINGS

In order that the invention may be more readily understood, an example of the invention will be described below with reference to the accompanying drawings.

DESCRIPTION OF THE PREFERRED EMBODIMENTS

Figure 4:
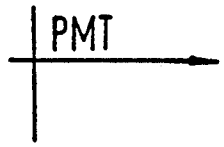
FIG. 4 is a timing diagram illustrating various heart and pacer events as well as various time intervals relevant to the invention.
Figure 4:
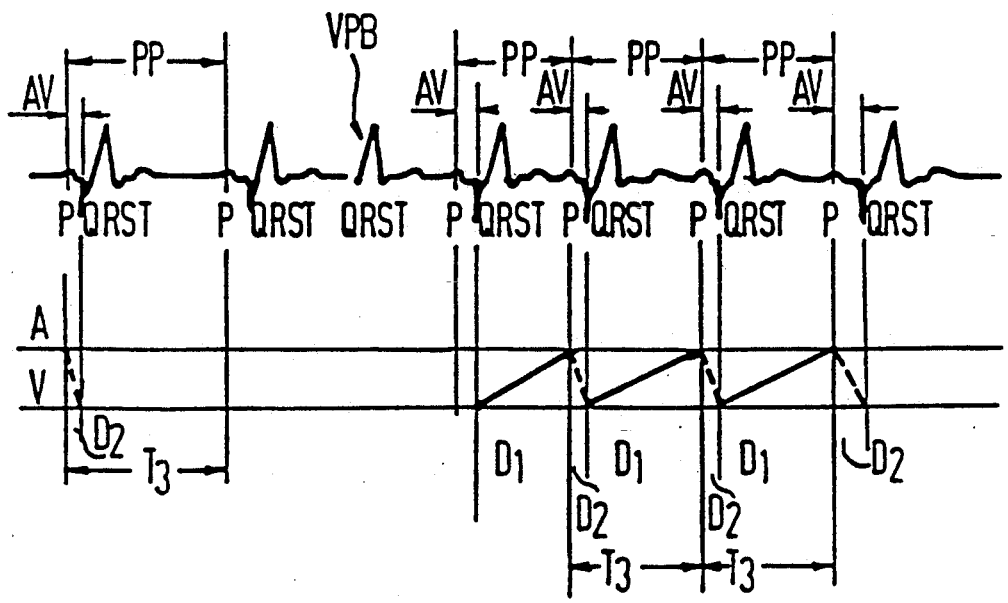

According to the invention, the pacemaker investigates the presence of a PMT by measuring the correlation between an interval $T_3$, for signals generated by the heart and an interval $D_2$, for signals generated by the pacemaker. Reference is now made to FIG. 4, where a non-PMT situation is illustrated to the left and a PMT situation is illustrated to the right. The lower part of the figure illustrates the atrial (A) and the ventricular (V) conduction levels and the dashed and the continuous lines indicate antegrade and retrograde conduction, respectively.

The cycle time of a PMT comprises two delay intervals, one ($D_1$) related to the retrograde heart tissue conduction, and the other one ($D_2$) related to the pacemaker introduced interval or time delay between atrial and ventricular activity (AV-interval). $D_1$ can be stable, vary regularly or stocastically. However, for short time periods, $D_1$ is limited and substantially constant. The Av-interval, $D_2$, is in this invention made to vary stocastically or in accordance with a predetermined pattern.

By varying the interval $D_2$ in a known way, the correlation between $D_2$ and $T_3$ is calculated for a short time period. Typically 2 to 6 heart cycles are needed to reach a reasonably safe decision that the value of the correlation exceeds a predetermined value and, consequently, that a PMT is present.

The high correlation for $D_2$ and $T_3$ when a PMT is present is explained by way of example below. Let the interval $T_3$ be the interval (PP) between two consecutive P-waves. If no PMT is present, the PP-interval is the interval between two spontaneous atrial beats, and the correlation between $D_2$ and $T_3$ is low as the PP-interval variation is independent of $D_2$. If, in contrast, a PMT is present, the PP-interval is the sum of the retrograde conduction interval $D_1$ and the pacemaker generated interval $D_2$. Consequently, during a PMT, there is a very high correlation between $D_2$ and $T_3$ (the PP-interval).

Alternatively, instead of using the PP-interval as $T_3$, quantities related thereto, for instance the atrial frequency or the interval between a ventricular stimulus and a P-wave, could be employed. In the last case, it is obvious that the expression "signals generated by the heart", previously used in connection with $T_3$, is intended to comprise signals related to ventricular stimuli, and further, that the correlation between $D_2$ and $T_3$ is contrary to where $T_3$ denotes the PP-interval.

Figure 1:
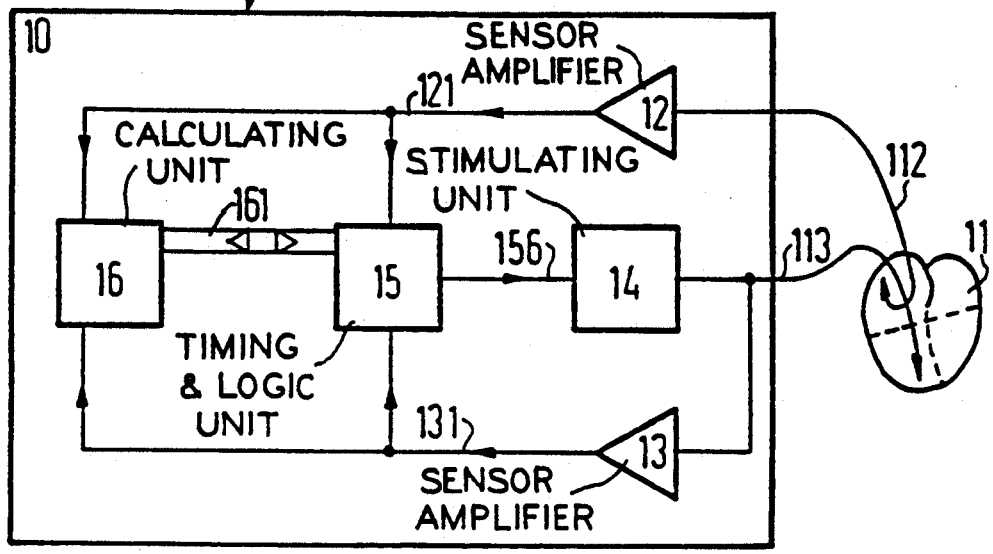
FIG. 1 is a functional block diagram of the pacemaker as connected to the heart.

In FIG. 1, the heart is designated 11 and the pacemaker is generally designated 10. The pacemaker 10 is connected to the heart through an electrode lead 112 for the atrium and an electrode lead 113 for the ventricle. The electrode leads 112 and 113 are respectively connected to signal sensors and amplifiers 12 and 13 for the atrium and the ventricle. The electrode lead (or possibly a further, separate electrode lead), not shown for the ventricle 113, is connected to a stimulating unit 14. The stimulating unit 14 delivers stimuli to the heart. A further stimulating unit (not shown), could possibly be provided for stimulating the atrium through electrode lead 112, or, anther through separate electrode lead (not shown). The basic pacemaker timing and logic unit 15 is controlled by the sensed signals applied thereto through leads 121 and 131. The sensed signals are related to spontaneous heart activities, viz. atrial P-wave or ventricular R-wave. If the heart fails to beat normally, stimulation pulses are emitted by the pacemaker in order to maintain the normal heart function. It is also possible to deliver correctly timed stimulation pulses even if spontaneous heart beats exist. The stimulation unit 14 is connected to the basic unit 15 through lead 156. The basic logic and timing unit 15 (to be described later) is connected to the calculating unit 16 (to be described later) through data bus 161.

Figure 2:
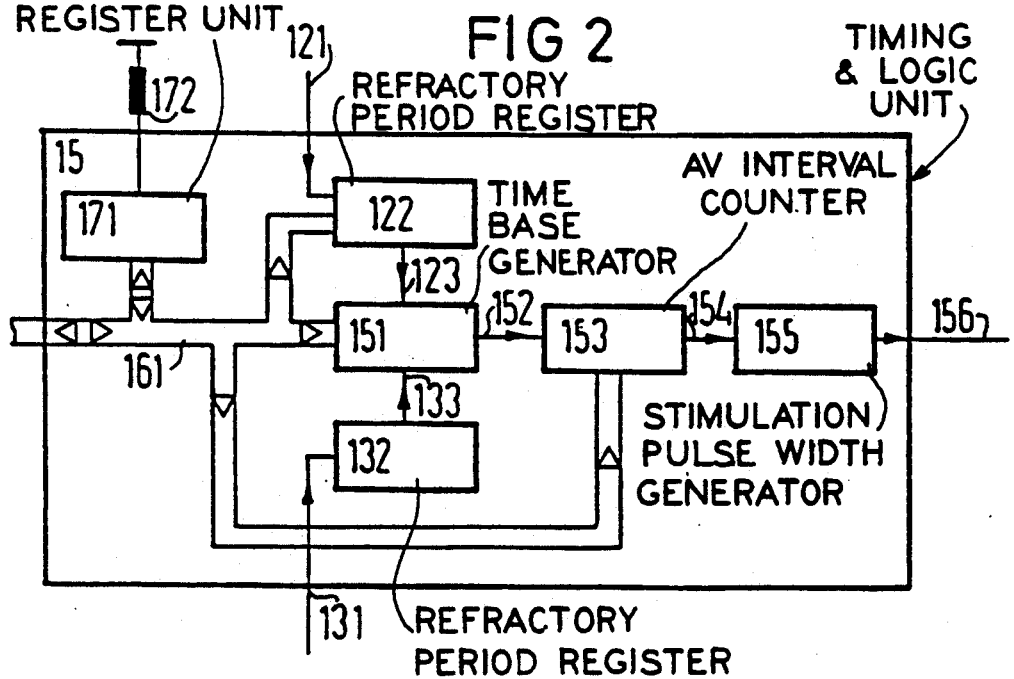
FIG. 2 is a functional block diagram of the pacemaker basic timing and logic unit 15.

In response to e.g. a sensed atrial signal on lead 121, the basic timing and logic unit 15 (FIG. 2) generates basic pacer escape intervals (PP-intervals) in the time base generator and time base register 151. A control signal on lead 152 triggers the AV-interval counter 153 simultaneously with the triggering of the time base generator 151. After the AV-interval has been timed out, a control signal on lead 154 triggers the stimulation pulse width generator and time register 155, generating a control signal on lead 156, which controls the stimulating unit 14. A further control circuit, similar to the one just described and also starting from the time base generator 151 but delivering stimuli for the atrium through electrode lead 112 or another separate (not indicated) electrode lead for the atrium can also be provided.

In order to prevent incorrect control due to false signal sensing after, for instance, a stimulation pulse has been delivered or a heart signal just sensed, the refractory period registers 122 and 132 and their respective leads 123 and 133 are provided in connection with atrial and ventricular signal sensing, respectively.

A communication and data register unit 171 is provided for the pacemaker programming and functional control. The communication is preferably carried out by telemetry means 172. The data bus 161 provides for the internal pacemaker transmission of programmed parameter values, control signals and time register values.

Figure 3:
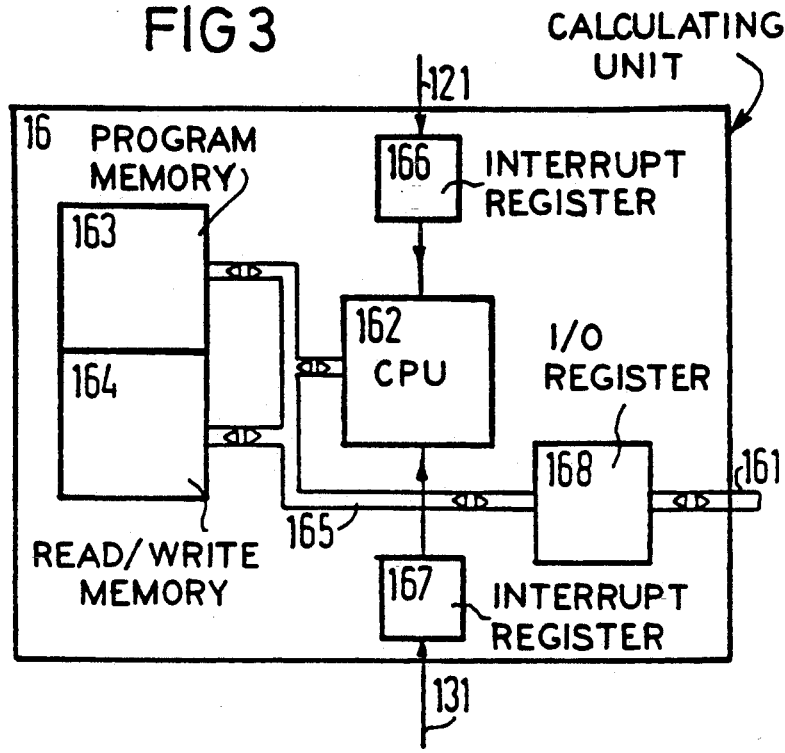
FIG. 3 is a functional block diagram of the calculating unit 16.

The calculating unit 16 (FIG. 3) comprises time registers, logic circuits and arithmetic processing circuits.

Preferably, a microprocessor is employed, and the microprocessor is operated in accordance with a correlation calculating program. Arithmetic processing, time measurement and control are then carried out from a RAM and ROM program memory 163 connected to a central processing unit (CPU) 162. Measured time intervals ($D_2$, $T_3$) and calculation results are stored in read-write memory 164. Detected atrial and ventricular signals are received via interrupt registers 166 and 167, respectively. Data from the microprocessor can be placed in the input-output register 168 via the internal bus 165 for subsequent communication with the basic timing and logic unit 15.

It should be noted that, for explanatory purposes, the timing and logic unit 15 and the calculating unit 16 have been disclosed as separate units. It is, however, possible to arrange unit 16 to carry out the functions of timing and logic unit 15.

The calculation of the correlation is carried out in accordance with well-known mathematical theory in the CPU 162, with interaction with the program memory 163 and the read/write memory 164, as needed, and can be made in different ways.

As an example, the mean value and the deviation from the mean value is calculated for each interval $T_3$ and each interval $D_2$, respectively. The deviation for each interval $T_3$ and for each corresponding interval $D_2$ are multiplied and the products added for all $T_3$, $D_2$ intervals. The resulting sum is then divided by the sum of the absolute values of the deviation for the $D_2$ intervals. If the result of this division exceeds a predetermined value, a PMT is present.

The PMT decision can also be referred to two correlation levels. Below the lowest level, there is no PMT and above the highest, a PMT is present. A value between the two levels indicates that a decision cannot be made with the intervals available, and therefore further intervals $D_2$, $T_3$ should be included until a decision can be reached.

Another way of calculating the correlation would be to subtract $D_2$ from $T_3$ for each corresponding $D_2$, $T_3$ interval, calculate the mean value for the resulting differences and the deviation therefrom for each resulting difference. Correspondingly, the mean value and the deviations therefrom for the intervals $D_2$ are calculated. These last deviations are compared to the corresponding difference deviations, and, if substantially equal, the correlation is high.

Finally, for a reliable detection of a PMT, the variation in $D_2$ should be of the same magnitude or greater than the variation in $D_1$. However, the number of intervals are also of importance for the reliability, and should the variation in $D_1$ be greater than that in $D_2$, the number of intervals should be correspondingly increased.

Although modifications and changes may be suggested by those skilled in the art, it is the intention of the inventor to embody within the patent warranted hereon all changes and modifications as reasonably and properly come within the scope of his contribution to the art.

I claim as my invention:

1. A heart pacemaker comprising:
   sensing means for detecting atrial events in a heart beating in successive heart cycles;
   stimulating means for stimulating the ventricle of said heart, said atrial events and the stimulation of the ventricle constituting cardiac events;
   variable delay means for generating a variable time delay between the detection of an atrial event and the stimulation of the ventricle;
   time measuring means for measuring a time interval between consecutive cardiac events, at least one of said detected events being a natural heartbeat detected by said sensing means;
   calculating means for calculating the correlation between said time delay and said time interval measured by said time measuring means; and
   logic means for indicating the presence of a pacemaker-mediated tachycarida if the value of said correlation deviates from a predetermined value.

2. A pacemaker as claimed in claim 1 wherein said logic means is a means for identifying the presence of pacemaker-mediated tachycardia if the value of said correlation exceeds said predetermined value.

3. A pacemaker as claimed in claim 1 wherein said logic means includes means for determining that a pacemaker-mediated tachycardia is not present if the value of said correlation is below a further predetermined value, said further predetermined value being lower than said predetermined value.

4. A pacemaker as claimed in claim 3 wherein said calculating means is a means for calculating the correlation between the time delay and the sum of a plurality of time intervals measured by said time measuring means over a plurality of said consecutive atrial events, forming a plurality of said heart cycles, if the value of said correlation is between said predetermined value and said further predetermined value.

5. A pacemaker as claimed in claim 1 wherein said variable delay means is a means for varying said delay in accordance with a predetermined programmable pattern.

6. A pacemaker as claimed in claim 5 wherein said calculating means is a means for calculating the correlation between said time delay and said time interval measured by said time measuring means over at least two heart cycles.

7. A pacemaker as claimed in claim 1 wherein said time measuring means is a means for measuring the interval between consecutive P-waves.

8. A pacemaker as claimed in claim 1 wherein said calculating means comprises:
   means for calculating an average value for time delays and an average value for time intervals over a plurality of said heart cycles;
   means for determining a deviation of each time delay from said average value for time delays and a deviation each time interval from said average value for time intervals;
   means for multiplying said deviations for each time delay and each time interval to obtain products and for adding said products for all time delays and all time intervals to obtain a resulting sum;
   means for calculating the sum of the absolute value of said deviations of said time delays; and
   means for dividing said resulting sum by said sum of absolute values for supply to said logic means as said value of the correlation.

9. A pacemaker as claimed in claim 1 wherein said time measuring means is a means for measuring a time interval between a consecutive ventricular stimulation and a P-wave.

10. A pacemaker as claimed in claim 9 wherein said logic means includes means for determining that pacemaker-mediated tachycardia is not present if the value of said correlation exceeds a further predetermined value, said further predetermined value being higher than said predetermined value.

* * * * *

UNITED STATES PATENT AND TRADEMARK OFFICE
CERTIFICATE OF CORRECTION

PATENT NO. : 5,253,644
DATED : October 19, 1993
INVENTOR(S) : Hakan Elmqvist

It is certified that error appears in the above-indentified patent and that said Letters Patent is hereby corrected as shown below:

On the title page, item (19) and (75): Change the spelling of the last name of the inventor from "ELMVIST" to "ELMQVIST".

Signed and Sealed this

Twenty-sixth Day of April, 1994

*Attest:*

BRUCE LEHMAN

*Attesting Officer*     *Commissioner of Patents and Trademarks*